United States Patent
Rassman et al.

(10) Patent No.: US 7,126,688 B2
(45) Date of Patent: *Oct. 24, 2006

(54) MICROARRAY SCANNING

(75) Inventors: William Rassman, Los Angeles, CA (US); David Ralin, South Pasadena, CA (US); Robert A. Lieberman, Torrance, CA (US); Lothar U. Kempen, Redondo Beach, CA (US); Herbert Shapiro, Laguna Niguel, CA (US)

(73) Assignee: Maven Technologies, LLC, Los Angeles, CA (US)

( * ) Notice: Subject to any disclaimer, the term of this patent is extended or adjusted under 35 U.S.C. 154(b) by 119 days.

This patent is subject to a terminal disclaimer.

(21) Appl. No.: 10/847,754

(22) Filed: May 17, 2004

(65) Prior Publication Data

US 2005/0030535 A1 Feb. 10, 2005

Related U.S. Application Data

(63) Continuation-in-part of application No. 10/602,555, filed on Jun. 23, 2003, now Pat. No. 6,859,280, which is a continuation of application No. 09/614,503, filed on Jul. 11, 2000, now Pat. No. 6,594,011, and a continuation-in-part of application No. 10/046,620, filed on Jan. 12, 2002, now Pat. No. 6,833,920, which is a continuation-in-part of application No. 09/614,503, filed on Jul. 11, 2000, now Pat. No. 6,594,011, and a continuation-in-part of application No. 09/838,700, filed on Apr. 19, 2001, now Pat. No. 7,023,547, which is a continuation-in-part of application No. 09/614,503, filed on Jul. 11, 2000, now Pat. No. 6,594,011.

(51) Int. Cl.
  *G01J 4/00* (2006.01)
(52) U.S. Cl. .................................................... 356/369

(58) Field of Classification Search ................ 436/518; 356/445, 364–370; 385/12, 129
See application file for complete search history.

(56) References Cited

U.S. PATENT DOCUMENTS

| 4,238,565 A | | 12/1980 | Hornby et al. |
| 4,256,834 A | | 3/1981 | Zuk et al. |
| 4,508,832 A | | 4/1985 | Carter et al. |
| 5,164,589 A | | 11/1992 | Sjoedin |
| 5,229,833 A | * | 7/1993 | Stewart ..................... 356/364 |
| 5,255,075 A | | 10/1993 | Cush |
| 5,313,264 A | | 5/1994 | Ivarsson et al. |
| 5,437,840 A | * | 8/1995 | King et al. .............. 422/82.08 |
| 5,483,346 A | | 1/1996 | Butzer |

(Continued)

OTHER PUBLICATIONS

Tadashi Saitoh, et al. "Optical Characterization of Very Thin Hydrogenated Amorphous Silicon Films Using Spectroscopic Ellipsometry"; Japanese Journal of Applied Physics; vol. 30. No. 11B, Nov. 1991. pp. L1914-1916.

(Continued)

*Primary Examiner*—Gregory J. Toatley, Jr.
*Assistant Examiner*—Isiaka O. Akanbi
(74) *Attorney, Agent, or Firm*—MacPherson Kwok Chen & Heid LLP; David S. Park (57) ABSTRACT

Methods and apparatus for scanning of a microarray to provide an image of the microarray are disclosed. Data related to change in polarization state of a scanning light beam for individual points or lines or other portion of the microarray are collected and processed to image the microarray at high resolution and speed.

41 Claims, 4 Drawing Sheets

U.S. PATENT DOCUMENTS

| | | | |
|---|---|---|---|
| 5,485,277 A * | 1/1996 | Foster | 356/445 |
| 5,491,556 A * | 2/1996 | Stewart et al. | 356/445 |
| 5,573,956 A | 11/1996 | Hanning | |
| 5,593,130 A | 1/1997 | Hansson et al. | |
| 5,633,724 A * | 5/1997 | King et al. | 356/445 |
| 5,641,640 A | 6/1997 | Hanning | |
| RE35,716 E | 1/1998 | Stapleton et al. | |
| 5,753,518 A | 5/1998 | Karlsson | |
| 5,856,873 A * | 1/1999 | Naya et al. | 356/369 |
| 5,922,594 A | 7/1999 | Loefas | |
| 5,922,604 A | 7/1999 | Stapleton et al. | |
| 5,955,729 A | 9/1999 | Nelson et al. | |
| 5,965,456 A | 10/1999 | Malmqvist et al. | |
| 5,972,612 A | 10/1999 | Malmqvist et al. | |
| 6,008,010 A | 12/1999 | Greenberger et al. | |
| 6,008,893 A | 12/1999 | Roos et al. | |
| 6,026,053 A * | 2/2000 | Satorius | 365/235 |
| 6,045,996 A | 4/2000 | Cronin et al. | |
| 6,127,183 A | 10/2000 | Ivarsson et al. | |
| 6,140,044 A | 10/2000 | Bessemer et al. | |
| 6,143,513 A | 11/2000 | Loefas | |
| 6,143,574 A | 11/2000 | Karlsson et al. | |
| 6,197,595 B1 | 3/2001 | Anderson et al. | |
| 6,200,814 B1 | 3/2001 | Malmqvist et al. | |
| 6,207,381 B1 | 3/2001 | Larsson et al. | |
| 6,277,330 B1 | 8/2001 | Liu et al. | |
| 6,289,286 B1 | 9/2001 | Andersson et al. | |
| 6,493,097 B1 | 12/2002 | Ivarsson | |
| 6,503,760 B1 | 1/2003 | Malmqvist et al. | |
| D472,644 S | 4/2003 | Dawson et al. | |
| 6,589,798 B1 | 7/2003 | Loefas | |
| 6,594,011 B1 | 7/2003 | Kempen | |
| D480,149 S | 9/2003 | Dawson et al. | |
| 6,698,454 B1 | 3/2004 | Sjoelander et al. | |
| 2002/0019019 A1 | 2/2002 | Hamalainen et al. | |
| 2002/0154311 A1 | 10/2002 | Ivarsson | |
| 2002/0182717 A1 | 12/2002 | Karlsson | |
| 2003/0022388 A1 | 1/2003 | Roos et al. | |
| 2003/0067612 A1 | 4/2003 | Ivarsson | |
| 2004/0002167 A1 | 1/2004 | Andersson et al. | |
| 2004/0012676 A1 | 1/2004 | Weiner et al. | |
| 2004/0023247 A1 | 2/2004 | Xu et al. | |
| 2004/0030504 A1 | 2/2004 | Helt et al. | |
| 2004/0038268 A1 | 2/2004 | Pirrung et al. | |

OTHER PUBLICATIONS

"Handbook of Optics", Michael Bass Editor in Chief, by The Optical Society of America; vol. 1; pp. 4.23, 4.24; 1995 McGraw-Hill, Inc.

Bass et al. "Handbook of Optics", by The Optical Society of America; vol. 1; Section 41.10; 1995 McGraw-Hill, Inc.

Gang Jin et al. "Imaging Ellipsometry Revisited: Developments for Visualization of Thin Transparent Layers on Silicon Substrates", American Institute of Physics, Rev. Sci. Instrum., pp. 2930-2936, Aug. 1996.

Max Born et al. "Principles of Optics—Electromagnetic Theory of Propagation, Interference and Diffraction of Light", Sixth Edition, pp. 47-51 Pergamon Press.

Eggins, "Biosensors: An Introduction", pp. 112-113, 1987 John Wiley & Sons.

Danny Van Noort et al. "Monitoring Specific Interaction of Low Molecular Weight Biomolecules on Oxidized Porous Silicon Using Ellipsometry", Biosensors & Bioelectronics vol. 13, No. 3-4 pp. 439-449, 1998 Elsevier Science, S.A. Great Britain.

Gang Jin et al. "Imaging Ellipsometry Biosensors Applications" Transducers '95. Eurosensors IX, Digest of Technical Papers vol. 2, Sessions A7-D13, Papers No. 232-496 pp. 509-512, Stockholm, Sweden, Jun. 1995.

Jinyu Wang "Waveguide Ellipsometry Biosensors: Concept and Preliminary Analysis", SPIE vol. 1648, Fiber Optical Medical and Fluorescent Sensors and Applications pp. 44-50, 1992.

Ulf Jonsson et al. "Flow-Injection Ellipsometry—An in Situ Method for the Study of Biomolecular Adsorption and Interaction at Solid Surfaces," Colloids and Surfaces, 13 (1985) pp. 333-339, 1985 Elsevier Science Publishers BV, Amsterdam, The Netherlands.

Johnsson, Ulf et al. "Biosensors Based on Surface Concentration Measuring Devices-The Concept of Surface Concentration" Progress in Colloid and Polymer Sci. vol. 70, pp. 96-100, 1985.

Schena, Mark "DNA Microarrays: A Practical Approach" Edited by Mark Schena, Department of Biochemistry, Beckman Center, Stanford University Medical Center, Stanford, USA, Oxford University Press, 1999.

Schema, PhD. Mark, "Microarray Biochip Technology" TeleChem International. Inc., Sunnyvale, California, USA, A BioTechniques Books Publication, Eaton Publishing, pp. 10-11, 2000.

Harland G. Tompkin, et al. "Spectroscopic Ellpsometry and Reflectometry A User's Guide" A Wiley-Interscience Publication, John Wiley & Sons, Inc., 1999.

Ulf Jonsson et al. "Surface Immobilization Techniques in Combination with Ellipsometry" Methods in Enzymology vol. 137, Immobilized Enzymers and Cells Part D pp. 381-1351, 1988 Academic Press, Inc. Harcourt Brace Jovanovich, Publishers.

CH Streibel et al. "Characterization of Biomembranes by Spectral Ellipsometry, Surface Plasmon Resonance and Interferometry with Regard to Biosensor Application", Biosensors & Bioelectronics 9, pp. 139-146, 1994, 1994 Elsevier Science Publishers Ltd.

T, A. Ruzgas et al., "Ellipsometric Immunosensors for the Determination of γ-Interferon and Human Serum Albumin", Biosensors & Bioelectronics 7, pp. 305-308, 1992 Elsevier Science Publishers Ltd.

Haken Nygren et al. "Determination by Ellipsometry of the Affinity of Monoclonal Antibodies", Journal of Immunological Methods, 92, pp. 219-225, 1986 Elsevier Science Publishers Ltd.

John F. Place et al. "Opo-electronic Immunosensors: A Review of Optical Immunoassay At Continuous Surfaces", Biosensors 1, pp. 321-353, 1985 Elsevier Applied Science Publishers Ltd., England.

A. Brecht et al. "Biosensors: Fundamentals, Technologies and Applications" GBF Monographs, vol. 17, pp. 174-178, 1991 Germany.

Hakan Nygren et al. "Kinetics of Antibody-Binding to Surface-Immobilized Antigen: Influence of Mass Transport on the Enzyme-Linked Immunosorbent Assay (ELISA)", Journal of Colloid and Interface Science, vol. 107, No. 2 pp. 560-566, Oct. 1985 Academic Press, Inc.

Martin Malmsten et al. "Effects of Hydrophilization and Immobilization on the Interfacial Behavior of Immunoglobulins", Journal of Colloid and Interface Sicence 177, pp. 70-78, 1996 Academic Press, Inc.

Pentti Tengvall et al. "Temporal Studies on the Deposition of Complement on Human Colostrum IgA and Serum Immobilized on Methylated Silicon", Journal of Biomedical Materials Research, vol. 35, pp. 81-91, 1997 John Wiley & Sons, Inc.

Huaiyou Wang et al. "Assembly of Antibodies in Lipid Membranes for Biosensor Development", Applied Biochemistry and Biotechnology, vol. 53 pp. 163-181, 1995 Humana Press Inc.

G. Elender et al. "Wetting and Dewetting of Si/SiO2-Wafers by Free and Lipid-Monolayer Covered Aqueous Solutions Under Controlled Humidity", Journal de Physique, II France 4 pp. 455-479, Mar. 1994.

C.F Mandenius et al. "Coupling of Biomolecules to Silicon Surfaces for use in ellipsometry and other related technigues", Methods in Enzymology, vol. 137, pp. 389-394, 1988 Academic Press, Inc.

A.W. Flounders et al. "Patterning of Immobilized antibody layers via photolithography and oxygen plasma exposure", Biosensors and Bioelectronics, vol. 12, No. 6 pp. 447-456, 1997 Elsevier Science Ltd., Great Britain.

A. Ahluwalia et al. "A comparative study of protein immobilization techniques for optical immunosensors", Biosensors and Bioelectronics 7, (1991) pp. 207-214, 1992 Elsevier Science Publishers Ltd.

Dr. Rudolf Oldenbourg "Metamorph Imaging System", http://www.image1.com/products/metapolscope/ Universal Imaing Corporation Last Updated Jun. 10, 1999, pp. 1-2.

Dr. Rudolf Oldenbourg "A New view on polarization microscopy", Nature, vol. 381, pp. 811-812, Jun. 27, 1996.

Clifford C. Hoyt et al. "Structural analysis with quantitative birefringence imaging", American Laboratory, pp. 34-42, Jul. 1999.

Dirk Honig et al. "Direct visualization of monolayers at the air-water interface by Brewster angle microscopy", J. Phys. Chem., pp. 4590 & 4592, 1991 American Chemical Society.

S. Henon et al. "Microscope at the Brewster angle: direct observation of first-order phase transitions in monolayers", Rev. Sci. Instrum. 62, (4) pp. 936-939, Apr. 1991 American Institute of Physics.

Gang Jin et al. "A biosensor concept based on imaging ellipsometry for visualization of biomolecular interactions", Analytical Biochemistry 232, pp. 69-72, 1995.

Pentti Tengvalle et al. "Complement activation by 3-mercapto-1,2-propanediol immobilized on gold surfaces", Biomaterials vol. 17, No. 10 pp. 1001-1007, 1995 Elseviar Science Ltd., Great Britain.

H. Arwin "Spectroscopic ellipsometry and biology: recent developments and challenges", Thin Solid Films 313-314, pp. 7640774, 1998 Elsevier Science S.A.

Christopher Palmer "Diffraction Grating Handbook", pp. 35-44, 2000 Richardson Grating Laboratory, Rochester, New York.

Erwin G. Loewen "Diffraction Grating, Ruled and Holographic", Applied Optics and Optical Engineering, vol. IX, pp. 33-71, Bausch and Lomb, Inc., Rochester, New York 1983 Academic Press, Inc.

\* cited by examiner

MICROARRAY SCANNING

RELATED APPLICATIONS

This application is a continuation-in-part of U.S. patent application Ser. No. 10/602,555 filed on Jun. 23, 2003, now U.S. Pat. No. 6,859,280, which in turn is a continuation of U.S. patent application Ser. No. 09/614,503, filed on Jul. 11, 2000, now U.S. Pat. No. 6,594,011.

This application is also a continuation-in-part of U.S. patent application Ser. No. 10/046,620 filed on Jan. 12, 2002, now U.S. Pat. No. 6,833,920, which in turn is a continuation-in-part of U.S. patent application Ser. No. 09/614,503 filed on Jul. 11, 2000, now U.S. Pat. No. 6,594,011.

This application is also a continuation-in-part of U.S. patent application Ser. No. 09/838,700 filed on Apr. 19, 2001, now U.S. Pat. No. 7,023,547, which in turn is a continuation-in-part of U.S. patent application Ser. No. 09/614,503 filed on Jul. 11, 2000, now U.S. Pat. No. 6,594,011.

The above-mentioned U.S. patent application Ser. Nos. 10/602,555, 10/046,620, and 09/838,700, and U.S. Pat. No. 6,594,011 are incorporated by reference herein for all purposes.

BACKGROUND OF THE INVENTION

1. Field of Invention

This invention relates to imaging and scanning techniques and apparatus in conjunction with internal reflection at the boundary of an optically transparent material and more particularly to the use of such techniques and apparatus for detecting the presence, composition, quantity, and/or spatial distribution of substances on optically transparent substrates.

2. Discussion of the Related Art

This invention relates to imaging or scanning of a biochip (also referred to as a gene chip, protein chip, microarray and others). The formation of an array of biologically or chemically active spots on the surface of a substrate for identifying constituents in test material brought into contact with the array is well known. Typically, such processes require spots of, for example, oligonucleotides, cloned DNA, antibodies, peptides, receptors, enzymes, inhibitors, etc. which are processed to exhibit fluorescence, electroluminescence, current change, voltage change, etc. for providing a detectable signature for the presence of constituents in the material being tested.

An apparatus and method which provide for microarray scanning at high resolution and speed is needed and desirable for imaging of the microarray.

SUMMARY

Scanning methods and apparatus may be used to accumulate and process data regarding change in polarization state for individual points or lines or other portion of the microarray to image the microarray at high resolution and speed.

The total internal reflection at any point within the cross-section of the light beam causes a phase shift between the light component polarized in the plane of incidence and the component polarized perpendicular to the plane of incidence. The reflected light is detected by a polarization-sensitive detector such as a two dimensional array detector and the signal from this detector is then processed in a computer to provide information about substances on the surface of the specimen. Spatially distributed changes in polarization state over the microarray are indicative of the substances in the location in the specimen array corresponding to a position in the detector.

In accordance with one embodiment of the present disclosure, an apparatus for scanning is provided, comprising a light source emitting a polarized light beam, and an optical assembly having a surface adapted to allow placing thereon a specimen array, the light beam from the light source being reflected by the surface to provide an evanescent field over a portion of the specimen array such that the portion of the specimen array in the evanescent field causes a polarization change in the light beam. The apparatus further includes a detector positioned to detect the polarization change in the light beam as the light beam is scanned over the specimen array.

In accordance with another embodiment of the present disclosure, an apparatus for scanning is provided including a processor to process a plurality of signals related to spatially distributed polarization changes to thereby provide feedback for subsequent scanning of the specimen array.

In accordance with yet another embodiment of the present disclosure, a method of imaging is provided, comprising passing a polarized light beam into an optical structure for reflection at a surface of the optical structure to provide an evanescent field over a portion of a specimen array, the portion of the specimen array in the evanescent field causing a polarization change in the light beam. The method further includes detecting the polarization change in the light beam as the light beam scans the specimen array, and processing a plurality of signals related to spatially distributed polarization changes to thereby provide an image of the specimen array.

In accordance with yet another embodiment of the present disclosure, a method of scanning is provided, including processing a plurality of signals related to spatially distributed polarization changes to thereby provide feedback for subsequent scanning of the specimen array.

The apparatus and method of the present disclosure are especially adapted for imaging or scanning material in an aqueous solution. It is furthermore particularly suited for detecting attachment and detachment of analytes to a two-dimensional biomolecular array positioned on a light reflection surface as part of a molecular thin film system. In various applications a plurality of discrete specimen spots are presented in an array, where the method and apparatus will image or scan the array so as to distinguish each of the discrete specimen spots. Advantageously, fluorescence or molecular tagging is not necessary but optional for use in this invention.

These and other features and advantages of the present invention will be more readily apparent from the detailed description of the embodiments set forth below taken in conjunction with the accompanying drawings.

BRIEF DESCRIPTION OF DRAWINGS

Use of the same reference symbols in different figures indicates similar or identical items. It is further noted that the drawings may not be drawn to scale.

DETAILED DESCRIPTION

The invention comprises a method and apparatus for analyzing a two-dimensional arrangement of chemical substances with an imaging or scanning technique. A polarized light beam of known polarization state is directed into an optical assembly, for example a total internal reflection member (TIR member), configured for reflection at a light reflection surface, for example a total internal reflection surface (TIR surface), and then exits the optical assembly. In the context of this document, superposition of reflections as encountered at a layered optical structure where the layer thicknesses are smaller than the coherence length of the illuminating light is referred to as a single reflection.

The chemical specimen is in place on or above the light reflection surface in the evanescent field of the reflected light beam. After reflection, the beam is passed to a polarization-sensitive two-dimensional detector such as a polarizer and a camera or other types of detectors. The reflected beam's content can then be processed to determine the change in polarization state, locally in the two-dimensional cross-section of the beam. This provides a spatially distributed map of change of polarization state in the specimen. A variety of techniques are available to determine the change in polarization such as measuring the deviation from a null condition or by comparing the input polarization state to the output polarization state.

The refractive index composition of the materials within the evanescent field determines the change in the polarization state of the beam due to the reflection at the light reflection surface. A two-dimensional variation of this composition within the light reflection surface is associated with a respective variation of the polarization state spatially distributed across the cross-section of the reflected light beam.

In one application, the chemical specimen forms a two-dimensional array of molecules (referred to herein as receptors and generally referred to as capture agents or affinity agents) with specific affinities towards respective other molecules (referred to herein as ligands). In this application, the invention is utilized to indicate the presence or absence or rate of binding between ligands and receptors on the array. Such arrays commonly consist of a plurality of discrete specimen spots. The present method and apparatus images the array so as to distinguish each of the discrete specimen spots represented by the local change in polarization state in the cross-section of the reflected beam.

Subject to limitations in resolving power of the detector, the invention permits measurement of thickness and/or refractive index composition of the specimen under investigation with a very high resolution, in the sub angstrom range, spatially resolved over an entire area. It is noted that thickness and refractive index measurements are functions of the electronics of the detector and that spatial resolution is a function of the optics associated with the optical assembly. The invention is particularly useful in applications where the specimen is in an aqueous solution. In a particular application, the present invention is used to determine the presence of biological agents in a solution such as in immunosensor applications by measuring their attachment to antibodies on the TIR surface in the evanescent field. In another application, the present invention is used to determine the presence and structure of nucleic acid sequences in a solution by measuring their attachment to other nucleic acid sequences on the light reflection surface in the evanescent field. Described in more detail below are different embodiments of the invention.

Figure 1:
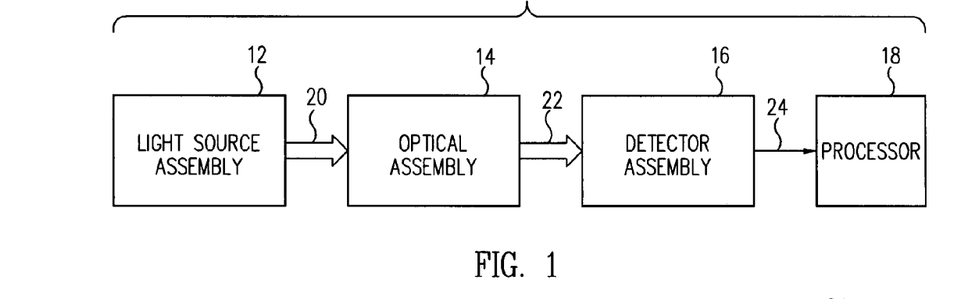
FIG. 1 is a block diagram of an illustrative system in accordance with the principles of this invention.
Figure 2:
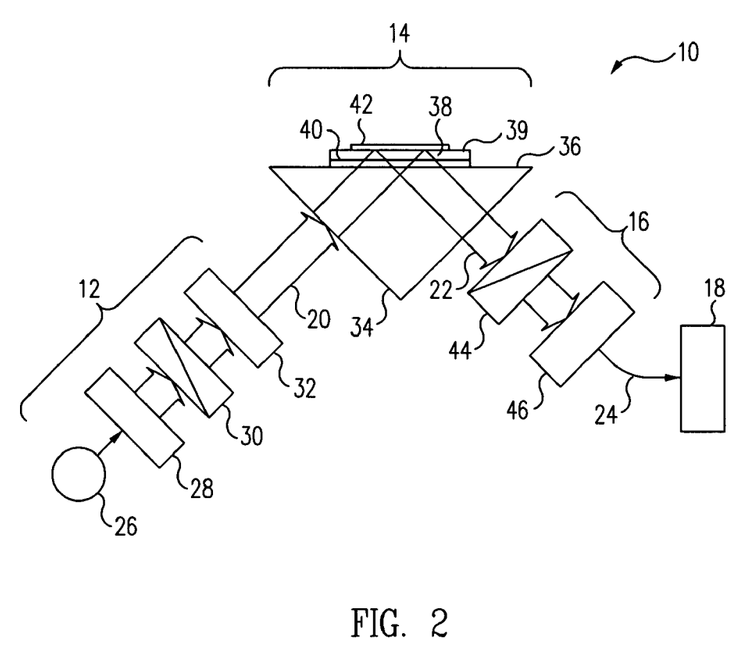
FIG. 2 is a block diagram of an embodiment of the system of FIG. 1.

FIGS. 1 and 2 show an apparatus which implements one embodiment of the invention. As shown in FIG. 1, the apparatus 10 can be described conveniently as consisting of three general portions. A first portion includes a polarized light source assembly 12, a second portion includes an optical assembly 14 providing a control layer and/or a light reflection surface, and a third portion includes a polarization-sensitive imaging detector assembly 16 which can employ for example a two-dimensional array detector.

Data from detector assembly 16 is sent by an electrical signal along a connector 24 to processor 18 such as a specially programmed computer and user access system including an image display. Data can be presented as an image, a data table, a graph, or in other forms. The polarized light source assembly 12 passes polarized light of known polarization state 20, which may be varied or varying to optical assembly 14 where a light beam reflection occurs. Reflected light 22, having a changed polarization state, passes to detector assembly 16, where it is recorded spatially over the cross-section of the beam. The recorded data is sent to processor 18 where the change of polarization state is determined to provide a spatially resolved map of changes in polarization state. Where the specimens are presented as an array of discrete spots, each spot will be imaged for its change in polarization state within the spot area.

FIG. 2 shows a more detailed schematic block diagram of a preferred embodiment. The polarized light source assembly 12 has a light source 26, a beam forming member 28 (if the nature of the light source is such as to make beam forming useful or necessary), a polarizer 30, and an optical retarder 32.

The optical assembly 14 has an optical element 34 which has an optical surface 36. Also shown is a control layer 38 over optical surface 36, and between them an index matching substance 40. A specimen 42 is positioned on light reflection surface 39 of control layer 38 in one example.

In one embodiment of the invention, optical element 34 is a prism configured along with control layer 38 in relationship to the incoming light beam 20 and the exiting light beam 22 such that the beam reflects only a single time at light reflection surface 39 and then exits the prism. If the specimen is placed directly on the optical surface 36, then the optical surface 36 would be the light reflection surface. But this is not the usual application, since the specimen (such as a biochip) is usually prepared more conveniently on a specimen slide and placed in the apparatus. In one example, control layer 38 with light reflection surface 39 can act as a specimen slide or control layer 38 can operate in conjunction with a specimen slide. However constructed, the invention incorporates an optical structure having a light reflection surface and the beam reflects at the reflection surface between entering and leaving the optical structure. In other words, there is a light reflection surface in optical contact with the specimen, such that the evanescent field associated with the total internal reflection interacts with the specimen.

In one embodiment, the post-reflection detector assembly 16 has a polarizer 44 and an imaging detector, for example a two-dimensional array detector 46 and preferably a camera of the CCD or CMOS array type. The processor 18 is a specially programmed computer (or processor) and output means for processing the imagery into a representation of film thickness variations spatially resolved over the cross-section of the area imaged. The imaging is acquired by detecting changes spatially distributed in the local polarization state in the beam's cross-section caused by the total internal reflection. This provides information about the presence and composition in the array of substances on the substrate surface for each resolvable point on the surface. Different polarization state changes are included in the cross-section of the reflected beam indicative of the substances on the specimen in the location in the specimen array corresponding to a position in the detector.

Processor 18 receives the data as an electrical signal (on connector 24) and characterizes the change of polarization state spatially over the two-dimensional array. In processor 18, the analysis and processing is done in one embodiment by comparing the known polarization state of the incoming light from the light source assembly 12 with the changed polarization state of the reflected light 22, spatially resolved two-dimensionally within the beam which provides a map of spatially distributed points or spots in the specimen array. The polarization shift is then analyzed by processor 18 to provide information of the presence and properties of elements in the chemical specimen. Other known techniques, such as null processing can be used to determine the change in polarization state.

Alternatively, light source 26 may be an LED, an SLD (Super Luminescent Diode), an incandescent light source, or a laser. If an LED or SLD is used, the set-up shown in FIG. 2 is appropriate, where the beam-forming member 28 is a collimator. If an incandescent light source is used, an optical filter is also used. In one embodiment, light source 26 for the apparatus is a quasi-monochromatic light source of moderate bandwidth. In accordance with the invention light source 26 is preferably an LED of moderate bandwidth. Preferably the bandwidth is a full width half maximum wavelength in the range of about 10 nm–50 nm, and more preferably a full width half maximum wavelength in the range of about 30 nm–50 nm.

In an alternative embodiment, optical retarder 32 can be placed instead to receive the exiting light beam 22 at a location before polarizer 44.

Figure 3:
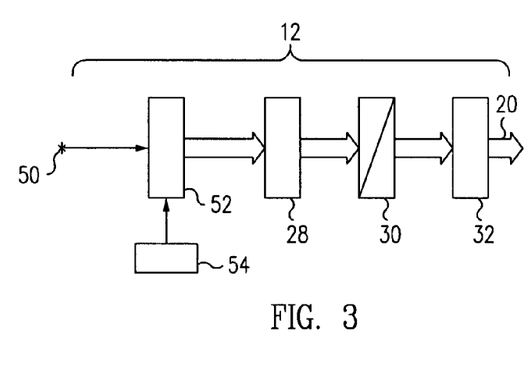
FIGS. 3, 4, and 5 are block diagrams of alternative portions of the system of FIG. 1.

FIG. 3 shows an additional embodiment. In embodiments in which the light source is a laser 50, a moving diffuser 52 is adapted to produce speckle-offsetting fluctuation of the minima and maxima in the speckle pattern caused by the laser. The moving diffuser 52 is attached to a mechanical actuator 54 which is preferably a motor and servo-apparatus for providing the speckle offsetting fluctuations. The light beam then proceeds through the beam-forming element 28, the polarizer 30, and the optical retarder 32, exiting light source assembly 12 as light beam 20.

Polarizer 30, in embodiments as shown in FIGS. 2 and 3, employs a polarizer of selected known polarization state. Polarizer 30 may be of the type having a mechanical actuator driven by a motor control signal so as to enable the variation and selection of the polarization state of the light beam 20.

As mentioned above, the optical element 34 (of FIG. 2) either alone or in combination with an index-matched substance may be arranged for use with a specimen in various ways to define an optical assembly so long as the specimen is in the evanescent field of the reflected beam.

As noted above, the specimen 42 (of FIG. 2) could be set directly on the optical surface 36 in which case the optical surface 36 would be the light reflection surface. But this is inconvenient and repeated use is likely to degrade the optical quality of the optical surface 36. Therefore, consistent with common practice in which a biochip or other chemical assay specimen is provided, a specimen slide or other supporting apparatus is employed. It is common in a biochip to provide an array of discrete specimen spots supported on a structure for obtaining analysis of each spot. The term total internal reflection optical element refers to known optical elements alone or in combination with other elements which provide the phenomenon known as total internal reflection. FIG. 2 shows use of a prism combined with a control layer 38 having a light reflection surface 39.

Figures 4, 5:
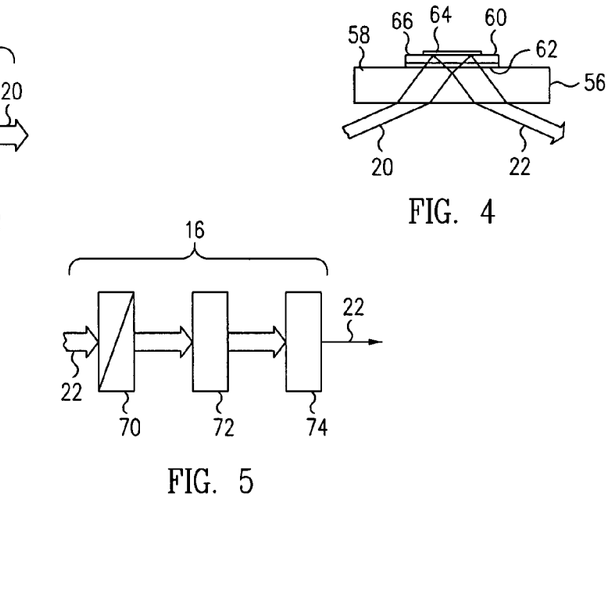

FIG. 4 shows an alternative optical arrangement in which a control layer 60 is placed above an index matching substance 62, which in turn is placed above a flat optical member 56 having an upper surface 58. A specimen 64 is mounted above a light reflection surface 66, which in one example is the top of control layer 60. The beam 20 enters the optical assembly, is refracted as it enters, and leaves optical member 56 after a single reflection at light reflection surface 66. Other mechanisms for providing total internal reflection and an evanescent field can be employed in practicing this invention as long as the specimen is placed so as to be in the evanescent field associated with the reflection.

As seen in FIG. 5, the post-reflection detector assembly 16 through which the beam 22 passes can alternatively consist of a polarizer member 70, a beam forming member 72, and an imaging detector 74 such as a two dimensional array detector or other type of imaging detector.

The method and apparatus of the present invention can be used in combination with biochips of the type having discrete specimen spots or a micro-titer plate containing an array of discrete spots or locations for analysis, where the detected change in polarization state is spatially related to the discrete locations in the reflected beam. Therefore, as used herein the control layer and specimen refers to any type of chemical or biological array that is desired to be examined. The foregoing described apparatus and methods are especially beneficial for imaging materials in an aqueous medium.

The invention as described above provides an extremely sensitive optical imaging system for real-time imaging of the binding status of biochip array elements on the surface of an optically transparent material such as a glass or plastic chip. An exemplary monitored array of a 15 mm square inscribed in a 20 mm circular field, with discrete specimen spots of size commensurate with the lateral resolution of the imaging optics, results in fully parallel, continuous real-time readout of up to 5 million sensor fields. Sensor sensitivity to surface attachment is in the femtogram/mm.sup.2 range (e.g., one DNA per square micron).

The apparatus of FIG. 1 operates by imaging the pattern of reactions on the biochip. Those reactions produce changes in the height, surface concentration, and/or refractive index of the material that reacts at each spot. The area imaged could be the entire biochip array or a portion of the entire biochip array. By providing an array of spots of different materials, different constituents in test material flowed over the spots bind in a manner which identifies those constituents. By including in a computer memory the positions of the various materials in the different spots of the array, the image produced by the apparatus of FIG. 1 identifies the constituents in the test material and can also determine the rate at which the reactions occur by imaging successively over time. With the apparatus described, height differences can be imaged dynamically over such short periods of time that intermediate height change readings can be recorded and therefore height change rates can be determined as well as allowing comparison of the rate of height change or intermediate amount of height change among the spots on the biochip array.

In another embodiment, an image of a microarray may be obtained by scanning a light beam over the microarray and detecting a polarization change in the light beam for each portion of the array that is interrogated. After exposing the array to molecules of interest under selected test conditions, scanning devices can examine a preselected portion of the array and determine a polarization change at that location. The portion of the array examined may encompass a variety of areas, including in one example an array spot or an equivalent area associated with a pixel or a plurality of pixels of an image, but is at least a resolvable point. Thus, scanning is another method of obtaining a spatially distributed map of polarization changes over a microarray to thereby provide a 2-dimensional image of the microarray.

Figure 6:
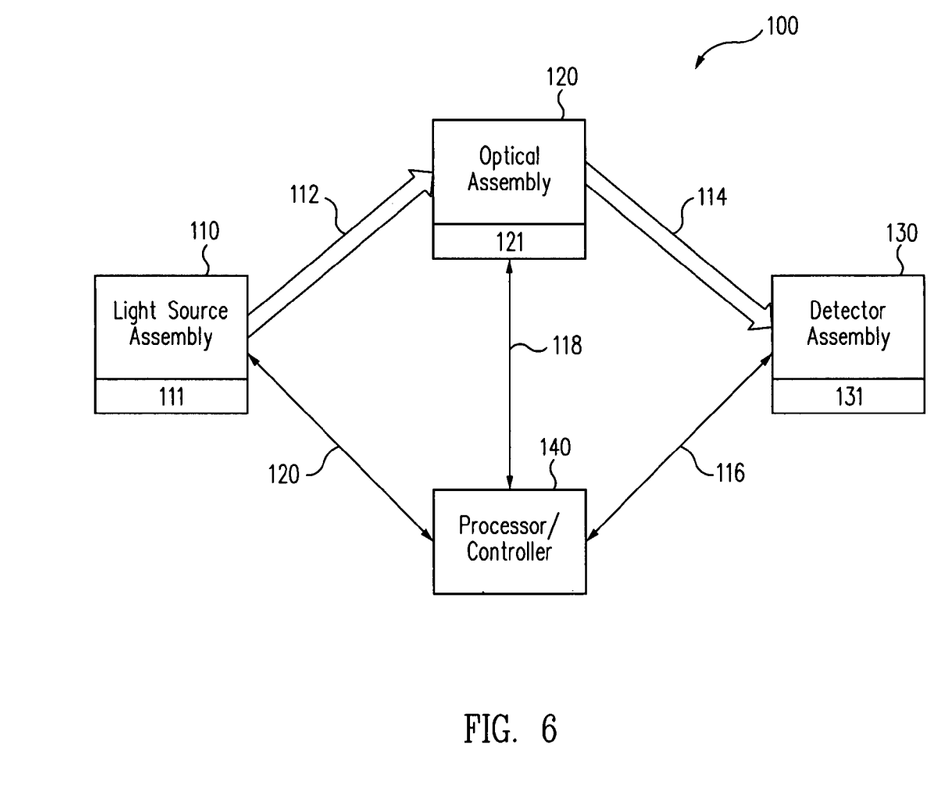
FIG. 6 is a block diagram of an embodiment of a scanning system and apparatus in accordance with the present disclosure.

Referring now to FIG. 6, a scanning apparatus 100 includes a light source assembly 110, an optical assembly 120, a detector assembly 130, and a processor/controller 140 operably coupled together. Light source assembly 110, optical assembly 120, detector assembly 130, and processor/controller 140 may be similar to the respective devices described above in conjunction with FIGS. 1–5 with additions or alterations as noted below.

In one embodiment, light source assembly 110 may include a light source for providing a light beam 112, and a focusing system with focusing optics for directing the light beam from the light source to the reflective surface of optical assembly 120. Light source assembly 110 directs the light beam at a portion of a microarray provided in conjunction with optical assembly 120 and moves the light beam in a scanning manner to interrogate other portions of the microarray. In other words, light source assembly 110 directs a light beam which rapidly scans the light beam back and forth across the reflective surface of optical assembly 120. It is apparent that typical zigzag patterns or other patterns across the microarray may be used to obtain data in a raster fashion.

In one example, the light source assembly may provide a light beam to a line (or other predetermined portion or section) of a microarray and scan a strip of the sample at a time. In another example, light source assembly may provide a laser beam to a spot having a diameter, defined as 1/e2 or the diameter at which intensity is 13.5% of peak, of 3 to 5 microns at any point within a flat field.

It is noted that a variety of devices may be employed to generate the sweeping motion of the light beam. In one example, rotating polyhedral mirrors may be employed to scan the light beam across the microarray. In a further example, the light source assembly may also direct the laser beam using a galvanometer mirror that scans the light beam across the surface of the reflective surface of the optical assembly. As used herein, the term "galvanometer" refers to devices that employ a servo motor to oscillate or rotate a mirror over a restricted, predefined range. This generates a rapidly sweeping or rastering beam reflecting from the galvanometer mirror, which is then directed at and swept across the surface of the reflective surface that is to be scanned. Typically, an optical train may be employed between the light source and the galvanometer mirror to assist in directing, focusing, or filtering the beam directed at and reflected from the galvanometer mirror.

In addition to providing smaller spot size while not sacrificing scanning field size, the focusing optics of the scanning system may include a telecentric objective lens. This allows undistorted imaging of the flat surface plane, across the entire scanning surface, i.e., regardless of where the input beam is propagating through the lens relative to the lens axis.

A multi-axis translation stage 121 may also move the microarray to position different portions of the microarray to be scanned while the light beam is stationary or moving. In one example, the translation stage moves the microarray at a constant velocity to allow for continuous integration and processing of data. Translation of the multi-axis translation stage can be managed by an appropriately programmed processor/controller 140 which may also control an auto-focus system.

Detector assembly 130 may be adapted to detect the polarization change of reflected light beam 114 as light beam 112 scans the microarray. The detector assembly may be similar to that previously described above but must be capable of detecting light beams that are scanned across the microarray.

It has been appreciated that very slight variation in the tilt or angle of a slide/microarray to be scanned must be accounted for in order to achieve acceptable focus on successive features to accurately obtain data. Systems may actuate a lens of the light source assembly or the translation stage carrying the microarray by servomechanism(s) to bring features into focus by varying the distance between the items. In other words, a control algorithm attempts to hold focus by maintaining the distance between a lens and slide despite asymmetries present in the system. Known feedback logic controllers may be used to accomplish this goal, including Proportional-Integral and Proportional-Integral-Derivative electronic feedback controllers. Auto-focusing features to maintain the sample in the focal plane of the light beam throughout the scanning process may be included with the light source assembly (e.g., actuator 111), the optical assembly (e.g., translation stage 121), and/or the detector assembly (e.g., actuator 131).

Thus, it is advantageous to maintain the same internal reflection angle for each resolvable point on the surface, whether the interrogation of the surface is with an expanded beam and an imaging detector, or by means of a single-beam scanning system with either a single-beam detector such as a photomultiplier tube (PMT) or an imaging detector such as a CCD. To maintain the same internal reflection angle, the incident angle should remain consistent, both with respect to the surface of interest and temporally, as the surface is repeatedly interrogated throughout a dynamic process.

Temporal consistency is more critical to maintain and is achieved through stable collimation or with critically consistent beam-steering and translation apparatus. Although perfect collimation of any source is not practical, ordinary collimation methods well known in the art provide sufficient consistency in maintaining the reflection angle to provide results with high resolution and accuracy. Moreover the angles within the beam do not change temporally. For a beam-steering scanning system, the beam-steering apparatus should be configured so that the angular deviations are minimal by locating the steering apparatus at a distance from the reflection point so that the surface is addressed with minimal angle deviations, or by including additional steering optics to maintain the angle as the surface is scanned. In one example, the reflection angle may be maintained by translating the illumination source within a plane located at the desired angle relative to the reflecting surface plane, or vice versa. Corresponding means (e.g., actuators, translation stages, servomechanisms, lenses, and mirrors) may apply to the detector as well. In the case where angle deviations are calculable and significant, the processing computer (e.g., processor/controller 140) accounts for such deviations.

A processor/controller 140 connected to detector assembly 130 is adapted to be capable of processing the data of scanned changes in polarization state as a function of a position on the reflective surface of the optical assembly and/or as a function of time. Once a portion of the microarray has been scanned, the data representing the portion of the microarray may be stored in the memory of a computer associated with processor/controller 140. As a result, the processor can provide a map of polarization changes spatially distributed over the microarray to thereby provide a 2-dimensional image of the microarray.

Processor/controller 140 is also operably coupled to light source assembly 110 via line 120, optical assembly 120 via line 118, and detector assembly 130 via line 116, to provide control over the scanning of the microarray with feedback information related to increasing or decreasing the resolution or frequency of scanning over a portion or portions of the microarray. Moreover, processor/controller 140 may be used to control auto-focusing features associated with light source assembly 110, optical assembly 120, and/or detector assembly 130.

Scanning time may be saved by adjusting the area or resolution of the area to be scanned in each pass. If it is predetermined that an area of the surface is not of interest, it saves time to not scan or to decrease the resolution of scanning in those areas. Similarly, if during a time-resolved dynamic process it is observed that areas are not demonstrating change, they may be omitted from subsequent scans or the resolution of scanning in those areas may be reduced. Conversely, areas of greater interest may be scanned with greater resolution and/or higher frequency if required or desired. A "fast and crude" or low-resolution scan may be employed until the areas of interest are identified. A signal processing algorithm or user intervention may implement these means of increasing scan speed, increasing concentration on areas of interest, and reducing data load.

Figure 7:
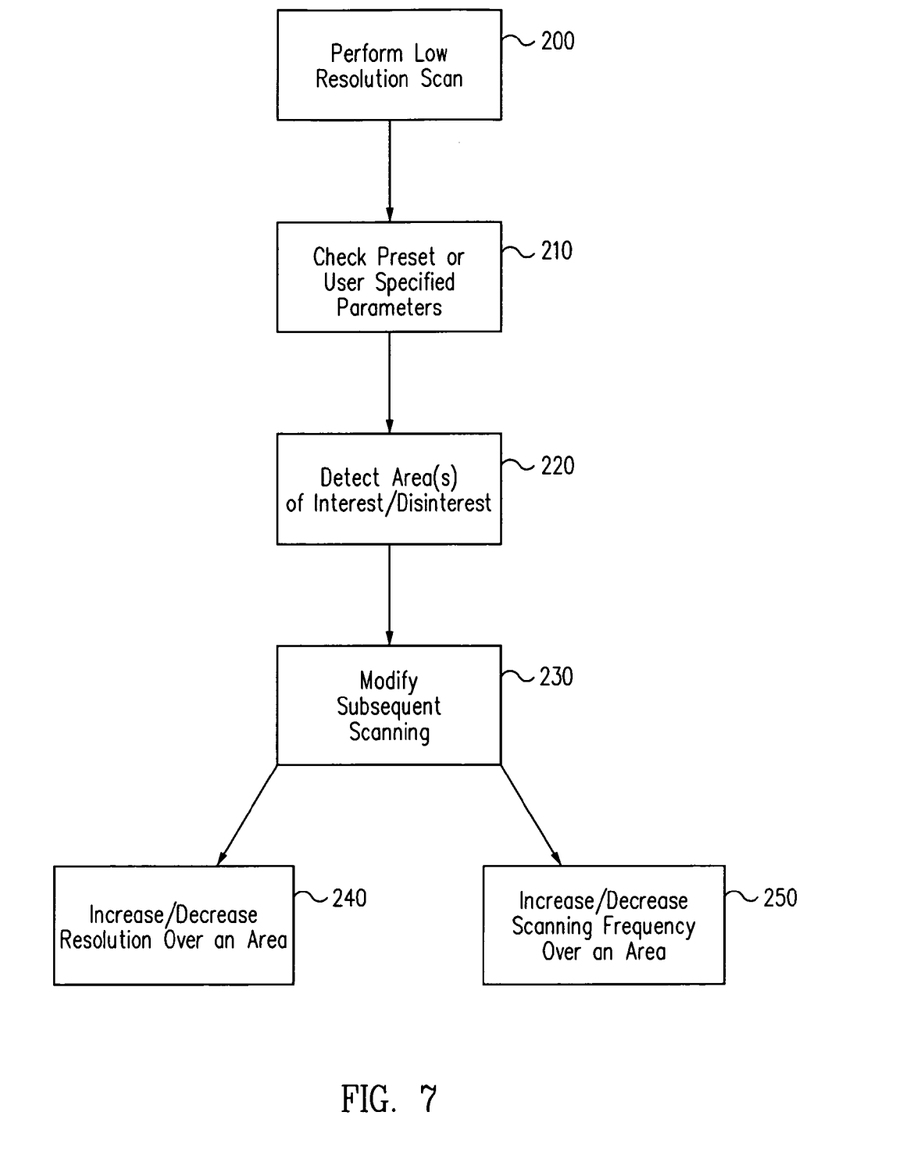
FIG. 7 is a flow chart of an embodiment of a scanning method in accordance with the present disclosure.

One embodiment of a scanning method is illustrated in the flowchart of FIG. 7. At a first state 200, a low resolution scan over the entire microarray may be provided. At a state 210, the data from the low resolution scan is processed and compared to a preset or user set of parameters so as to detect any area or areas of interest or disinterest over the microarray as shown by state 220. In one example, such a preset or user set of parameters may include feedback information for modification of subsequent scans based upon the size of an area of change and/or the intensity of change over time. At a state 230, after the detection of an area or areas of interest or disinterest, subsequent scanning over the area or areas of interest or disinterest are modified based upon the feedback information as specified by the preset or user set of parameters. In one example, at a state 240, the subsequent scan may be modified to increase or decrease resolution over the area or areas of interest or disinterest. In another example, at a state 250, the subsequent scan may be modified to increase or decrease the scanning frequency over the area or areas of interest or disinterest.

Although reference is made to biochips in the examples above, the procedure and the results apply generally to chemically sensitive materials on a light reflection surface.

The invention has been described above in terms of a prism having a light reflection surface, and having on the surface an array of molecular spots. In another embodiment, also described above, the array is formed on a separate slide or control layer positioned on the prism with index matching fluid between them so that only the upper surface of the slide or control layer forms the light reflection surface.

The above-described embodiments of the present invention are merely meant to be illustrative and not limiting. Various changes and modifications may be made without departing from this invention in its broader aspects. Accordingly, the invention is not limited to particular structures, dimensions, or process parameters. Therefore, the appended claims encompass all such changes and modifications as falling within the true spirit and scope of this invention.

We claim:

1. An apparatus for scanning, comprising:
   a light source emitting a polarized light beam;
   an optical assembly having a surface adapted to allow placing thereon a specimen array, the light beam from the light source being reflected by the surface to provide an evanescent field over a portion of the specimen array such that the portion of the specimen array in the evanescent field causes a polarization change in the light beam; and
   a detector positioned to detect the polarization change in the light beam as the light beam is scanned over the specimen array.

2. The apparatus of claim 1, wherein the light source comprises a quasi-monochromatic light source of moderate bandwidth.

3. The apparatus of claim 2, wherein the quasi-monochromatic light source of moderate bandwidth is a light-emitting diode (LED) or a superluminescent diode (SLD).

4. The apparatus of claim 2, wherein the quasi-monochromatic light source of moderate bandwidth comprises an incandescent source and an optical filter, the light emitted from the incandescent source passing through the optical filter, the optical filter limiting the wavelengths of the light transmitted through the optical filter such as to constitute quasi-monochromatic light of moderate bandwidth.

5. The apparatus of claim 1, wherein the light source comprises a laser emitting substantially coherent light, and further comprising an optical diffuser mechanically attached to a mechanical actuator, the light emitted from the laser passing through the diffuser, the diffuser being moved with respect to the laser by the actuator, the movement of the diffuser with respect to the laser creating fluctuations in the speckle pattern of light detected by the detector, the fluctuations being adapted to remove speckle effects from the light detected by the detector.

6. The apparatus as in claim 5, wherein the mechanical actuator is a motor rotating the optical diffuser.

7. The apparatus of claim 1, wherein the light source comprises a beam forming system, the beam forming system causing the light emerging from the light source to be collimated.

8. The apparatus of claim 1, wherein the light source comprises an optical polarizer.

9. The apparatus of claim 8, wherein the optical polarizer is controllably rotated by a motor.

10. The apparatus of claim 1, wherein the light source comprises an optical retarder, the retarder introducing an optical phase shift between two orthogonal components of light passing through the retarder.

11. The apparatus of claim 10, wherein the optical retarder is controllably rotated by a motor.

12. The apparatus of claim 10, wherein the optical retarder changes retardance according to an externally introduced physical parameter.

13. The apparatus of claim 1, wherein the optical assembly comprises an optical prism.

14. The apparatus of claim 1, wherein the specimen array comprises a two-dimensional array formed of multiple fields comprising biomolecular substances.

15. The apparatus of claim 14, wherein the biomolecular substances are proteins, peptides, and/or polynucleotide sequences.

16. The apparatus of claim 1, wherein the detector comprises a two-dimensional array detector.

17. The apparatus of claim 16, wherein the detector comprises an optical polarizer, a two-dimensional CCD array, and/or a two-dimensional photodiode array.

18. The apparatus of claim 1, wherein the light beam is in the form of a line.

19. The apparatus of claim 1, further comprising a translation stage operably coupled to the optical assembly.

20. The apparatus of claim 1, further comprising an actuator operably coupled to the light source.

21. The apparatus of claim 1, further comprising an actuator operably coupled to the detector.

22. The apparatus of claim 1, further comprising a processor coupled to the detector, the processor processing the signal from the detector to obtain a representation of the optical phase shift occurring in the portion of the specimen array.

23. The apparatus of claim 1, further comprising a processor coupled to the detector, the processor processing a plurality of signals related to spatially distributed polarization changes as the light beam scans the specimen array to thereby provide an image of the specimen array.

24. The apparatus of claim 23, wherein the processor provides feedback to reduce or increase resolution over a portion of the microarray.

25. The apparatus of claim 23, wherein the processor provides feedback to skip scanning over a portion of the microarray.

26. The apparatus of claim 23, wherein the processor provides feedback to increase the frequency of scanning over a portion of the microarray.

27. An apparatus for scanning, comprising:
a light source emitting a polarized light beam;
an optical assembly having a surface adapted to allow placing thereon a specimen array, the light beam from the light source being reflected by the surface to provide an evanescent field over a portion of the specimen array such that the portion of the specimen array in the evanescent field causes a polarization change in the light beam;
a detector positioned to detect the polarization change in the light beam as the light beam is scanned over the specimen array; and
a processor to process a plurality of signals related to spatially distributed polarization changes to thereby provide feedback for subsequent scanning of the specimen array.

28. The apparatus of claim 27, wherein the processor provides feedback to reduce or increase resolution over a portion of the microarray.

29. The apparatus of claim 27, wherein the processor provides feedback to skip scanning over a portion of the microarray.

30. The apparatus of claim 27, wherein the processor provides feedback to decrease or increase the frequency of scanning over a portion of the microarray.

31. A method of imaging, comprising:
passing a polarized light beam into an optical structure for reflection at a surface of the optical structure to provide an evanescent field over a portion of a specimen array, the portion of the specimen array in the evanescent field causing a polarization change in the light beam;
detecting the polarization change in the light beam as the light beam scans the specimen array; and
processing a plurality of signals related to spatially distributed polarization changes to thereby provide an image of the specimen array.

32. The method of claim 31, further comprising using the plurality of spatially distributed polarization changes to determine two-dimensionally distributed presence and/or properties of the specimen array constituents.

33. The method of claim 31, wherein the specimen array is in a micro-titer plate.

34. The method of claim 33, further comprising:
resolving the plurality of spatially distributed polarization changes for matching positions in the micro-titer plate; and
analyzing the polarization changes to determine desired characteristics in each position.

35. The method of claim 31, wherein the specimen array is a series of discrete specimen spots.

36. The method of claim 35, further comprising analyzing the polarization changes to determine the binding characteristics of each discrete specimen spot.

37. The method of claim 31, wherein a specimen array having no molecular tagging is placed in the evanescent field.

38. A method of scanning, comprising:
passing a polarized light beam into an optical structure for reflection at a surface of the optical structure to provide an evanescent field over a portion of a specimen array, the portion of the specimen array in the evanescent field causing a polarization change in the light beam;
detecting the polarization change in the light beam as the light beam scans the specimen array; and
processing a plurality of signals related to spatially distributed polarization changes to thereby provide feedback for subsequent scanning of the specimen array.

39. The method of claim 38, wherein the subsequent scanning decreases or increases resolution over a portion of the microarray.

40. The method of claim 38, wherein the subsequent scanning skips over a portion of the microarray.

41. The method of claim 38, wherein the subsequent scanning decreases or increases the frequency of scanning over a portion of the microarray.

* * * * *